United States Patent [19]
Nakamura et al.

[11] Patent Number: 5,466,801
[45] Date of Patent: Nov. 14, 1995

[54] PROCESS FOR THE PREPARATION OF 3-, 6-SUBSTITUTED 2,5-MORPHOLINEDIONES

[75] Inventors: Charles E. Nakamura, Claymont; Robert Di Cosimo, Wilmington, both of Del.; John R. Moran, Charleston, S.C.

[73] Assignee: E. I. Du Pont de Nemours and Company, Wilmington, Del.

[21] Appl. No.: 110,602

[22] Filed: Aug. 26, 1993

Related U.S. Application Data

[63] Continuation of Ser. No. 923,705, Jul. 31, 1992, abandoned.

[51] Int. Cl.$^6$ .................................................. C07D 265/32
[52] U.S. Cl. ................................................. 544/173
[58] Field of Search ..................................... 544/173

[56] References Cited

U.S. PATENT DOCUMENTS

| | | | |
|---|---|---|---|
| 4,441,496 | 4/1984 | Shalaby et al. | 128/335 |
| 4,916,209 | 4/1990 | Fung et al. | 528/403 |
| 5,326,887 | 7/1994 | Di Cosimo et al. | 549/274 |

OTHER PUBLICATIONS

Chadwick et al., J. Am. Chem. Soc. 65, 392 (1943).
Cook et al., J. Chem. Soc., 2347 (1949).
Heider et al., Makromol. Chem., Rapid Commun. 6, 9 (1985).
Yonezawa et al., Makromol. Chem., Rapid Commun. 6, 607 (1985).
in't Veld et al., Makromol. Chem. 191, 1813 (1990).
Rumsch et al., FEBS Letters 9, 64 (1970).
Obrecht and Heimgartner, Helv. Chim. Acta 70, 329 (1987).
Hartwig et al., Liebigs Ann. Chem., 1952 (1982).
Ridge et al., J. Chem Soc., Perkin I, 2041 (1972).
Nissen et al., Makromol. Chem., Suppl. 1, 23 (1975).
Yasutake et al., FEBS Letters 100, 241 (1979).
Shemyakin et al., Zh. Obshch. Khim 42, 2320 (1972).

*Primary Examiner*—Robert W. Ramsuer

[57] ABSTRACT

A process for the preparation of 3- and/or 6-substituted 2,5-morpholinediones is disclosed. Such morpholinediones are useful as precursors for the preparation of depsipeptide polymers and copolymers.

16 Claims, No Drawings

PROCESS FOR THE PREPARATION OF 3-, 6-SUBSTITUTED 2,5-MORPHOLINEDIONES

This is a continuation of application Ser. No. 07/923,705, filed Jul. 31, 1992 now abandoned.

FIELD OF THE INVENTION

The present invention provides a process for the preparation of 3- and/or 6-substituted 2,5-morpholinediones. Said substituted 2,5-morpholinediones are useful as precursors for the preparation of depsipeptide polymers and copolymers.

BACKGROUND OF THE INVENTION

This invention provides a process for the preparation of 3- and/or 6-substituted 2,5-morpholinediones represented by Formula I where each R is independently H, $C_1$–$C_{12}$ hydrocarbyl or $C_1$–$C_{12}$ substituted hydrocarbyl and at least one R is $C_1$–$C_{12}$ hydrocarbyl or $C_1$–$C_{12}$ substituted hydrocarbyl.

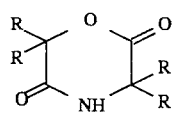

Compounds of Formula I are useful as precursors for the preparation of depsipeptide polymers and copolymers. Depsipeptides are cyclic polypeptides in which some amide nitrogens are replaced with oxygen. Ring-opening polymerizations or copolymerizations of 2,5-morpholinedione derivatives give polydepsipeptides of high molecular weight. These degradable polymers are particularly useful for applications where programmed lifetime of the polymer product is desirable. For example, applications include, but are not limited to, bioabsorbable medical implant devices such as sutures.

2,5-Morpholinedione derivatives have been prepared from N-(α-haloacyl)-α-amino acid salts. Chadwick and Pacsu obtained 6-methyl-2,5-morpholinedione by sublimation from alkaloid and sodium salts of (α-bromopropionylglycine (J. Am. Chem. Soc. 65, 392 (1943)). Similarly, Cook and Cox prepared various 2,5-morpholinedione derivatives with alkyl substituents at the 3-, 4- and/or 6-positions (J. Chem. Soc., 2347 (1949)). More recently, unsubstituted and 3-, 4- and/or 6-alkyl substituted 2,5-morpholinediones, suitable for polymerization, have been prepared from the appropriate N-(α-haloacyl)-α-amino acid salts by sublimation from the heated salt (Shalably and Koelmel, U.S. Pat. No. 4,441,496, Heider et al., Makrotool. Chem., Rapid Commun. 6, 9 (1985), Yonezawa et al., Makromol. Chem., Rapid Commun. 6, 607 (1985), in't Veld et al., Makromol. Chem. 191, 1813 (1990)) or by reaction in solution (Fung and Glowaky, U.S. Pat. No. 4,916,209 (EP 322154;1989) ). Rumsch et al. prepared (L)-3-phenylmethyl-2,5-morpholinedione by treating N-bromoacetyl-(L)-phenylalanine with silver oxide in dioxane (FEBS Letters 9, 64 (1970)).

Obrecht and Heimgartner prepared diamides of Formula II (where $R^1$=H, methyl, phenylmethyl, or phenyl) from α-hydroxy carboxylic acids and 3-(dimethylamino)-2,2-dimethyl-2H-azirine which when treated in solution with HCl gave 6,6-dimethyl-, 6-phenylmethyl-, and 6-phenyl- (but not 6,6-diphenyl-) derivatives of 3,3-dimethyl-2,5-morpholinedidone (Helv. Chim. Acta 70, 329 (1987)).

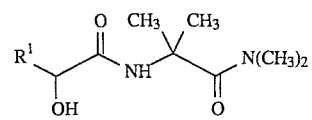

3,6-Disubstituted 2,5-morpholinediones were prepared by treating a chloroform/toluene solution of N-(α-hydroxyacyl) amino acids with methanesulfonic acid in a Soxhlet apparatus containing 3A molecular sieves (Hartwig and Schöllkopf, Liebigs Ann. Chem., 1952 (1982)).

2,5-Morpholinediones derivatives have also been prepared from O-(α-aminoacyl)-α-hydroxy carboxylic acid derivatives of Formula III where $R^2$=H or alkyl and C(O)X corresponds to the N-hydroxysuccinimide ester, pentachlorophenyl ester, acid azide, or acid chloride (Ridge et al., J. Chem Soc., Perkin I, 2041 (1972); Nissen et al., Makromol. Chem., Suppl. 1, 23 (1975); Yasutake et al., FEBS Letters 100, 241 (1979); and Shemyakin et al., Zh. Obshch. Khim 42, 2320 (1972)).

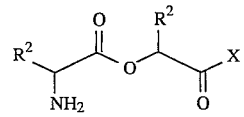

In each case, the compounds of Formula III were obtained by condensation of N-protected amino acids (e.g., benzyloxycarbonyl) with α-hydroxy carboxylic acid derivatives followed by a deprotection step.

The processes described above may be used in the preparations of 3- and/or 6- substituted 2,5-morpholinediones, however, they require time consuming substrate preparation and costly purification procedures in order to recover pure product.

SUMMARY OF THE INVENTION

The present invention provides a process for making 2,5-morpholinediones of the structure:

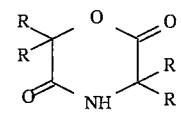

wherein each R is independently hydrogen, $C_1$–$C_{12}$ hydrocarbyl or $C_1$–$C_{12}$ substituted hydrocarbyl and at least one R is $C_1$–$C_{12}$ hydrocarbyl or $C_1$–$C_{12}$ substituted hydrocarbyl, by reacting an ester or free acid of an N-(α-hydroxyacyl)-α-amino acid substrate of the structure:

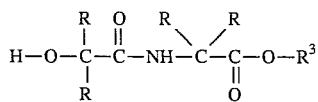

wherein each R and $R^3$ is independently hydrogen, $C_1$–$C_{12}$ hydrocarbyl, or $C_1$–$C_{12}$ substituted hydrocarbyl and at least one R is $C_1$–$C_{12}$ hydrocarbyl or $C_1$–$C_{12}$ substituted hydrocarbyl, over a fixed bed catalyst the reaction being carried out at about 150° C. to about 350° C. followed by collection of the product.

Also disclosed is a process for making optically active 3- and/or 6-substituted 2,5-morpholinediones of the structure:

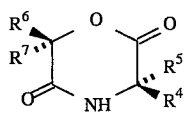

where:

a) $R^4$, $R^5$, $R^6$, and $R^7$ are independently H, $C_1$–$C_{12}$ hydrocarbyl or $C_1$–$C_{12}$ substituted hydrocarbyl and at least one R is $C_1$–$C_{12}$ hydrocarbyl or $C_1$–$C_{12}$ substituted hydrocarbyl; and b) the structure contains at least one chiral center, by reacting an ester or free acid of an N-(α-hydroxyacyl)-α-amino acid substrate of the structure:

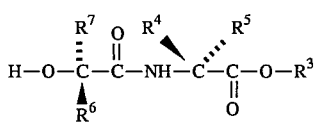

where $R^4$, $R^5$, $R^6$, and $R^7$ are defined above, $R^3$ is independently hydrogen, $C_1$–$C_{12}$ hydrocarbyl or $C_1$–$C_{12}$ substituted hydrocarbyl, the structure containing at least one chiral center, and is optically active. That reaction is carried out over a fixed bed catalyst, at about 150° C. to 350° C.

DETAILED DESCRIPTION OF THE INVENTION

The present invention provides a novel route for the production of 3- and/or 6-substituted 2,5-morpholinediones, represented by Formula I, where each R is independently H, hydrocarbyl or substituted hydrocarbyl, containing between 1 and 12 carbons and at least one R is hydrocarbyl or substituted hydrocarbyl. These substituted 2,5-morpholinediones are prepared by a vapor-phase pyrolytic ring closure of an ester or free acid of a N-(α-hydroxyacyl)-α-amino acid, represented by Formula IV, where R is defined as for Formula I and $R^3$ is H or hydrocarbyl or substituted hydrocarbyl containing between 1 and 12 carbon atoms, where the reaction takes place over a fixed bed catalyst system. The reaction is illustrated in Equation 1.

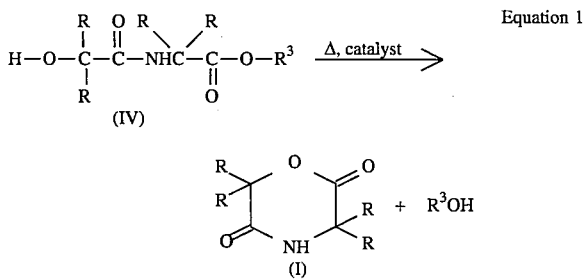

Equation 1

Suitable substrates for the process of the present invention are the ester or free acid of N-(α-hydroxyacyl)-α-amino acids (IV) where R and $R^3$ are defined above. Substrates for this process can be prepared by reaction of α-hydroxy carboxylic acids and esters of α-amino carboxylic acids with an appropriate coupling agent. For example, reaction of an α-hydroxy carboxylic acid, an ester of an α-amino carboxylic acid, and dicyclohexycarbodiimide by a standard procedure gives an ester of a N-(α-hydroxyacety)-α-amino acid in good yield. See Example 1 and Tothet al., Tetrahedron 48, 923 (1992). Protection of the hydroxyl group is not required. It is expected that free acids of N-(α-hydroxyacyl)-α-amino acids can be prepared by hydrolysis of their respective esters. Incorporation of optically active α-hydroxy carboxylic acids and/or esters of α-amino carboxylic acids into the substrate molecules lead to optically active 2,5-morpholinedione products, see Example 1.

Substrates suitable for the process of the present application will incorporate unsubstituted or mono or di-substituted glycolyl as the α-hydroxy carboxyl component. Similarly, substrates suitable for the process will incorporate unsubstituted or mono or di-substituted α-amino acids or their esters. Substrates which incorporate a naturally occurring α-amino acid moiety, drawn from the group consisting of but not limited to alanine, leucine, or phenylalanine are preferred and esters of N-(α-hydroxyacyl)-α-amino acids are most preferred. Ethyl esters are competent substrates which have the advantage of being easily and economically prepared. Additionally, increased yields and/or selectivities resulting from an increase in the reaction rate of Equation 1 may be obtained by utilizing an ester substrate where the pKa of the equivalent alcohol of $R^3$ is reduced compared to that of ethyl alcohol (p$K_a$=16). Preparation of the ester substrates may be accomplished by incorporating anion stabilizing groups into $R^3$ such as halide or acetylene. Most preferred are ester substrates of Formula IV where the equivalent alcohol of $R^3$ has a pKa of about 9 to 14 and where the equivalent alcohol of $R^3$ is selected from the group including but not limited to 2-chloroethyl alcohol, propargyl alcohol, or phenyl alcohol derivatives.

In the context of this disclosure and claims the term "Hydrocarbyl" refers to any alkyl, aralkyl, aryl or alkaryl group which may contain unsaturated and branched chains. "Substituted hydrocarbyl" refers to a hydrocarbyl group containing at least one of the groups consisting of halogen, ether, or oxo.

It is desirable to operate this process under conditions such that substrate and product are readily volatilized. As this depends, in part, on the molecular weight of the reaction components, the molecular weight of the substrate of Formula IV is limited by restricting each R and $R^3$ substitutent to contain no more than about 12 carbons.

In carrying out the process of the present invention, an ester or free acid of N-(α-hydroxyacyl)-α-amino acid (IV), either neat or dissolved in an inert solvent, is fed over a fixed-bed catalyst at an appropriate temperature. The reaction effluent is collected in a trap optionally containing a suitable solvent. The pure compounds of Formula I are then obtained by methods commonly utilized by those skilled in the art.

If a solution of a compound of Formula IV is used, it is essential that the solvent be inert. It is anticipated that any non-reactive solvent capable of withstanding temperatures up to 350° C. without degrading will serve as a suitable reaction solvent. Suitable solvents include, but are not limited to, tetrahydrofuran and toluene.

A variety of catalysts may be utilized in the process of the present application including zirconium oxide and titanium (IV) oxide and molecular sieves however, preferred catalysts are aluminum oxides containing 0–25% silicon dioxide, with surface areas greater than 1 m²/g. Optionally, a preheating zone consisting of a bed of crushed quartz chips can be present.

The process of the present application is operable at temperatures of between 150° and 350° C. The optimum temperature will, in part, depend upon the vapor pressure of the substrate since is desirable that reaction take place at temperatures where substrates and products are present predominantly in the vapor-phase.

A stream of inert gas is used to maintain a contact time between substrate and catalyst. Contact times may range between 0.1 and 10 seconds. The short contact time serves to minimize the undesired reactions, such as the addition of unreacted substrate to the labile 2,5-morpholinedione products. It is anticipated that any inert gas would be suitable for use in the process of the present application, including nitrogen, helium and argon where nitrogen is most preferred.

The reaction effluent is collected in a trap, optionally containing a suitable solvent cooled below 0° C. Solvents which may be used to collect the reaction effluent include, but are not limited to, tetrahydrofuran and toluene.

The compounds of Formula I provided by the process of the present application may be purified by methods known to those skilled in the art. For example, highly pure 2,5-morpholinedione products can be obtained by crystallization.

An important feature of this process is that it is performed in the vapor-phase since high dilution is obtained, favoring intramolecular cyclization of the substrate without the necessity of using large amounts of solvent. Furthermore, the elimination of competing intermolecular reactions allows the use of N-(α-hydroxyacyl)-α-amino acids and their esters as substrates, which would otherwise be expected to form a mixture of monomers and linear and cyclic oligomeric products.

The following examples are meant to illustrate the instant invention but are not meant to limit it in any way.

EXAMPLES

General Methods

A 69-cm length of 8-mm I.D./10 mm O.D. quartz tubing (Quartz Scientific, Inc.) was packed with 0.5–2.0 mL of catalyst using glass wool plugs which were optionally treated with Sigmacote® (Sigma Chemical Co.). The catalysts were: crushed quartz (Catalyst A); 80.3% α-$Al_2O_3$ and 17.9% $SiO_2$, 25–35 $m^2$/g, catalog #SA 3232 from Norton Co. (Catalyst B); and 99.5+% α-$Al_2O_3$, S.A. 0.04 $m^2$/g, catalog #13-0750 from Strem Chemicals, Inc. (Catalyst C). All catalysts were ground and screened to a mesh size of 28–35. The tubing was placed vertically in a Lindberg Model 55122-1 single zone tube furnace with a 30-cm heated zone, positioning the catalyst slightly above the middle of the heated zone. The top of the tubing was fitted with a T connecting the tubing to a Brooks Instruments mass flow controller calibrated for nitrogen at 1–120 mL/min and a syringe pump containing the substrate.

A solution of substrate in freshly distilled tetrahydrofuran or toluene was gravity fed into the fixed-bed reactor via a 22 gauge needle at a rate of 1 mL/hr along with a stream of dry nitrogen at a rate of between 20–120 mL/min (STP). The reactor was maintained at a constant temperature of between 180° and 300° C. The reactor effluent was collected for 4–5 hr in a solvent trap containing the same solvent as the feed cooled on dry ice. The contents of the trap were recovered along with any residue that collected on the lower portion of the tubing, the solvent was removed, and the residue was analyzed by $^1$H NMR. The weight and volume of crushed quartz, where used as a preheating zone, was not included in contact time or weight feed/weight catalyst/hr calculations.

EXAMPLE 1

Synthesis of 3-Methyl-2,5-morpholinedione by Pyrolysis of N-(Hydroxyacetyl)alanine Ethyl Ester N-(Hydroxyacetyl)alanine Ethyl Ester One equivalent each of hydroxyacetic acid (10.0 g), dicyclohexylcarbodiimide, (L)-alanine ethyl ester hydrochloride and imidazole was stirred in 500 mL acetonitrile. The reaction mixture, initially at 0° C. was allowed to warm to room temperature overnight and then heated at 65° C. for 2 hours. After the addition of an equal volume of toluene, the reaction mixture was filtered and the solvent removed by rotovaping from the filtrate to give crude product. An aliquot of the crude product was chromatographed on silica gel to give N-(hydroxyacetyl)alanine ethyl ester (61% yield). $^1$H NMR (300 MHz, DMSO-$d_6$/TMS): δ1.19 (t, 3H, J=7.1 Hz), δ1.31 (d, 3H, J=7.2 Hz), δ3.83 (s, 2H), δ4.09 (d×q, 2H, J=1.2 and 7.1 Hz, irradiation in the methyl region eliminates the smaller coupling constant), δ4.32 (d×q, 1H, J=7.3 and 7.3), and δ8.31 (br d, 1H, J=7.2 Hz). $^{13}$C NMR (75 MHz, CDCl$_3$/TMS): 13.59, 17.54, 47.31, 61.02, 61.48, and 172.17. $[\alpha]^{25}_D$=−4.1°±0.4° (c=1.99, CHCl$_3$). HRMS: calcd for $C_7H_{14}NO_4$ (M+H)$^+$, 176.0923; found, 176.0921.

Experiment 1

A 10% solution W/V in toluene of N-(hydroxyacetyl)alanine ethyl ester was passed through a quartz tube containing 1.0 mL of quartz (Catalyst A) on top of 0.5 mL of SA 3232 (Catalyst B). The feed flow rate was 1.0 mL/hr; nitrogen flow rate, 29 mL/min (STP); and, the reaction temperature, 300° C. Contact time (CT) and weight feed/ weight catalyst/hr (WWH) were 0.49 s and 2.75 hr$^{-1}$, respectively. Using heating tape, the two inches of tubing extending from the bottom of the furnace was maintained at 300° C. The reactor effluent was collected in two solvent traps connected in series and cooled in dry ice. After four hours, the reaction was terminated by stopping the flow of substrate and the reactor effluent was combined with material washed from the bottom of the tube. The recovered material was rotovaped and the resulting residue, along with a known amount of tert-butyl methyl ether, was analyzed by $^1$H NMR (DMSO-$d_6$). Conversion and selectivity were 92 and 50%, respectively.

Experiments 2–9

Experiments 2 through 9 were performed essentially as described in Experiment 1 except that the heating tape was omitted in Experiments 7 and 8. The results are given in Table 1. In some cases, crude 3-methyl-2,5-morpholinedione solidified in the quartz tube just below in heating zone.

An analytical sample of 3-methyl-2,5-morpholinedione was prepared from the reaction of Experiment 8 by crystallization from isopropanol. $^1$H NMR (300 MHz, DMSO-$d_6$/ TMS): δ1.33 (d, 3H, J=7.0), δ 4.30 (dq, 1H, J=1.0 and 6.9 Hz), δ4.61 (d, 1H, J=15.3 Hz), δ4.86 (d, 1H, J=15.4 Hz), and δ8.53 (br s, 1H). $^{13}$H NMR (75 MHz, DMSO-$d_6$): δ16.89, 47.85, 67.77, 165.91, and 169.09. $[\alpha]^{25}_D$=−14.8°±1.0° (c=2.04, acetone). HRMS: calcd for $C_5H_8NO_3$ (M+H)$^+$, 130.0504; found, 130.0507.

TABLE 1

| EXPERIMENT | CATALYST (mL) | TEMP °C. | CT (s) | WWH (1/hr) | CONVER (%) | SELECT (%) |
|---|---|---|---|---|---|---|
| | A/B (1/0.5) | 300 | 0.49 | 2.75 | 92 | 50 |

TABLE 1-continued

| EXPERIMENT | CATALYST (mL) | | TEMP °C. | CT (s) | WWH (1/hr) | CONVER (%) | SELECT (%) |
|---|---|---|---|---|---|---|---|
| 2 | A/B | (1/0.5) | 270 | 0.48 | 2.59 | 93 | 42 |
| 3 | A/B | (1/0.5) | 240 | 0.48 | 2.67 | 92 | 57 |
| 4 | A/B | (1/0.5) | 225 | 0.48 | 2.75 | 83 | 93 |
| 5 | A/B | (1/0.5) | 210 | 0.49 | 2.75 | 58 | 16 |
| 6 | A/B | (1/0.5) | 180 | 0.48 | 2.84 | 39 | 13 |
| 7 | A/B | (1/0.5) | 255 | 0.48 | 2.75 | 87 | 97 |
| 8 | A/B | (1/0.5) | 255 | 0.48 | 2.93 | 75 | ca. 100 |
| 9 | (C) | (2) | 300 | 1.94 | 0.28 | 43 | 0 |

EXAMPLE 2

Synthesis of 3-Isobutyl-2,5-morpholinedione by Pyrolysis of N-(Hydroxyacetyl)leucine Ethyl Ester N-(Hydroxyacetyl)leucine ethyl ester was prepared from hydroxyacetic acid and (L)-leucine ethyl ester hydrochloride by the method described in Example 1. $^1$H NMR (CDCl$_3$/TMS, 300 MHz): $\delta 0.95$ (d, 6H, J=5.9 Hz), $\delta 1.29$ (t, 3H, J=7.1 Hz), $\delta 1.59$–1.70 (m, 3H), $\delta 4.10$ (s, 2H), $\delta 4.19$ (q, 2H, J=7.1 Hz), $\delta 4.62$ (ddd, 1H, J=5.3, 8.5, and 8.8 Hz), and $\delta 7.1$ (br d, 1H, J=8.5 Hz). $^{13}$C NMR: (CDCl$_3$/TMS, 75 MHz): $\delta 13.97$, 21.72, 22.65, 24.74, 41.25, 50.26, 61.29, 61.86, 172.30, and 172.73. $[\alpha]^{25}_D = -4.0° \pm 0.4°$ (c=1.98, CHCl$_3$). HRMS: calcd for C$_{10}$H$_{20}$NO$_4$ (M+H)$^+$ 218.1392; found, 218.1390.

Solutions of N-(hydroxyacetyl)leucine ethyl ester (10% w/v in freshly distilled tetrahydrofuran) were treated essentially as described in Example 1, Experiment 1. The results are given in Table 2 below.

An analytical sample of 3-isobutyl-2,5-morpholinedione was obtained from Experiment 2. $^1$H NMR (CDCl$_3$/TMS, 300 MHz): $\delta 0.98$ (d, 3H, J=6.2 Hz, —CH$_3$), $\delta 1.00$ (d, 3H, J=6.3 Hz, —CH3), $\delta 1.71$ (ddd, 1H, J=4.3, 9.1 and 12.3 Hz, —CH(H—)), $\delta$approx. 1.81 (m, 1H, —CH(CH$_3$)$_2$), $\delta 1.88$ (ddd, 1H, J=4.7, 8.3 and 12.1 Hz, —CH(H)—), $\delta 4.15$ (ddd, 1H, J=2.4, 4.8 and 9.0 Hz, —NCH—), $\delta 4.77$ (s, 2H, —OCH$_2$—), and $\delta 7.82$ (1H, br s, NH). $^{13}$C NMR: (CDCl$_3$/TMS, 75 MHz): $\delta 21.60$, 23.01, 24.57, 41.88, 52.10, 67.59, 166.08, 167.20. HRMS: calcd for C$_8$H$_{17}$N$_2$O$_3$ (M+NH$_4$)$^+$ 189.1239; found, 189.1241.

ester hydrochloride by the method described in Example 1. $^1$H NMR (300 MHz, CDCl$_3$/TMS): $\delta 1.22$ (t, 3H, J=7.1 Hz), $\delta 3.09$ (dd, 1H, J=6.1 and 13.8 Hz), $\delta 3.15$ (dd, 1H, J=6.3 and 13.9 Hz), $\delta 4.02$ (s, 2H), $\delta 4.15$ (q, 2H, J=7.2 Hz ), $\delta 4.87$ (ddd, 1H, J=6.2, 6.2 and 8.2 Hz), and $\delta 7.09$–7.31 (6H, aromatic and NH). $^{13}$C NMR (75 MHz, CDCl$_3$/TMS): 14.24, 38.24, 52.95, 61.78, 62.18, 127.28, 128.71, 129.38, 136.90, 171.62, and 172.00. $[\alpha]^{25}_D = +44.3° \pm 0.4°$ (c=1.90, CHCl$_3$). HRMS: calcd for C$_{13}$H$_{18}$NO$_4$ (M+H)$^+$, 252.1236; found, 252.1236.

Solutions of N-(2-hydroxypropionyl)alanine ethyl ester (10% w/v in freshly distilled tetrahydrofuran) were treated essentially as described in Example 1, Experiment 1. The results are given in Table 3 below.

An analytical sample of 3-benzyl-2,5-morpholinedione was prepared from the reaction of Example 1 by crystallization from toluene: $^1$H NMR (300 MHz, CDCl$_3$/TMS): $\delta 3.21$ (d, 2H, J=5.3 Hz), $\delta 3.76$ (d, 1H, J=16.3 Hz), $\delta 4.42$ (d, 1H, J=16.4 Hz), $\delta 4.48$ (dt, 1H, J=2.4 and 5.1 Hz), and $\delta 7.18$–7.37 (aromatic and NH). $^{13}$C NMR (75 MHz, CDCl$_3$/TMS): 40.09, 55.14, 67.23, 128.25, 129.47, 129.91, 134.44, 165.77, and 166 40 HRMS: calcd for C$_{11}$H$_{15}$N$_2$O$_3$ (M+NH$_4$)$^+$, 223.1083; found, 223.1084.

TABLE 2

| EXPERIMENT | CATALYST (mL) | | TEMP (°C.) | CT (s) | WWH (1/hr) | CONVER (%) | SELECT (%) |
|---|---|---|---|---|---|---|---|
| 1 | A/B | (0.5/0.5) | 250 | 0.45 | 2.71 | 64 | 67 |
| 2 | A/B | (0.5/0.5) | 225 | 0.47 | 2.71 | 86 | 19 |

EXAMPLE 3

Synthesis of 3-Benzyl-2,5-morpholinedione by Pyrolysis of N-(Hydroxyacetyl)phenylalanine Ethyl Ester N-(Hydroxyacetyl)phenylalanine ethyl ester was prepared from hydroxyacetic acid and (L)-phenylalanine ethyl

TABLE 3

| EXPERIMENT | CATALYST (mL) | | TEMP (°C.) | CT (s) | WWH (1/hr) | CONVER (%) | SELECT (%) |
|---|---|---|---|---|---|---|---|
| 1 | A/B | (0.5/0.5) | 250 | 0.45 | 2.63 | 96 | 50 |

TABLE 3-continued

| EXPERIMENT | CATALYST (mL) | TEMP (°C.) | CT (s) | WWH (1/hr) | CONVER (%) | SELECT (%) |
|---|---|---|---|---|---|---|
| 2 | A/B (0.5/0.5) | 225 | 0.47 | 2.63 | 94 | 50 |

EXAMPLE 4

Synthesis of 3,6-Dimethyl-2,5-morpholinedione by Pyrolysis of N-(2-Hydroxypropionyl)alanine Ethyl Ester N- (2-Hydroxypropionyl) alanine ethyl ester was prepared from anhydrous (L)-lactic acid and (L)-alanine ethyl ester hydrochloride by the method described in Example 1. $^1$H NMR (300 MHz, CDCl$_3$/TMS): δ1.29 (t, 3H, J=7.2 Hz), δ1.41 (d, 3H, J=6.9 Hz), δ1.43 (d, 3H, J=7.2 Hz), δ3.86 (br s, 1H), δ4.20 (q, 2H, J=7.1 Hz), δ4.24 (q, 1H, J=6.8 Hz), δ4.55 (dq, 1H, J=7.3 and 7.3 Hz), and δ7.25 (br d, 1H, J=7.3 Hz). $^{13}$C NMR (75 MHz, CDCl$_3$/TMS): 14.25, 18.36, 21.08, 47.90, 61.70, 68.30, 173.14, and 174.86. $[\alpha]^{25}_D$=−19.6°±0.4° (c=2.00, CHCl$_3$). HRMS: calcd for C$_8$H$_{16}$NO$_4$ (M+H)$^+$, 190.1079; found, 190.1078.

Solutions of N-(2-hydroxypropionyl) alanine ethyl ester (10% w/v in freshly distilled tetrahydrofuran) were treated essentially as described in Example 1, Experiment 1. The results are given in Table 4 below.

An analytical sample of 3,6-dimethyl-2,5-morpholinedione was prepared from the reaction of Experiment 1 by crystallization from toluene.. $^1$H NMR (300 MHz, CDCl$_3$/TMS): δ1.58 (d, 3H, J=7.1 Hz), δ1.63 (d, 3H, J=7.1 Hz), δ4.23 (dq, 1H, J=ca 3 and 7.0 Hz), δ4.87 (q, 1H, J=7.1 Hz) δ7.92 (br s) and δ1.56 (d, 3H, J=6.9 Hz), δ1.60 (d, 3H, J=6.9 Hz), δ4.22 (q, 1H, J=6.9 Hz), δ4.88 (q, 1H, J=6.8 Hz), δ7.77 (br s) which correspond to isomers of 3,6-dimethyl-2,5-morpholinedione. $^{13}$C NMR (75 MHz, CDCl$_3$/TMS): 16.10, 17.00, 17.68, 18.81, 49.43, 49.50, 74.64, 75.20, 167.61, 168.58, 168.78, and 169.33. HRMS: calcd for C$_6$H$_{13}$N2O$_3$ (M+NH$_4$)$^+$, 161.0926; found, 161.0927.

TABLE 4

| EXPERIMENT | CATALYST (mL) | TEMP (°C.) | CT (s) | WWH (1/hr) | CONVER (%) | SELECT (%) |
|---|---|---|---|---|---|---|
| 1 | A/B (0.5/0.5) | 250 | 0.45 | 2.71 | 98 | 98 |
| 2 | A/B (0.5/0.5) | 225 | 0.47 | 2.71 | 78 | 46 |

What is claimed is:

1. A process for making 2,5-morpholinediones of the structure:

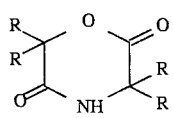

wherein each R is independently hydrogen, C$_1$–C$_{12}$ hydrocarbyl, or substituted hydrocarbyl and at least one R is C$_1$–C$_{12}$ hydrocarbyl or C$_1$–C$_{12}$ substituted hydrocarbyl, by reacting an ester or free acid of an N-(α-hydroxyacyl)-α-amino acid substrate of the structure:

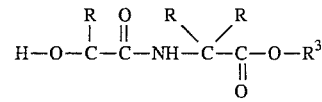

wherein each R and R$^3$ is independently hydrogen, C$_1$–C$_{12}$ hydrocarbyl or C$_1$–C$_{12}$ substituted hydrocarbyl and wherein at least one R is C$_1$–C$_{12}$ hydrocarbyl or C$_1$–C$_{12}$ substituted hydrocarbyl, over a fixed bed catalyst, wherein the catalyst has a surface area greater than 1 m$^2$/g, the reaction being carried out at about 150° C. to about 350° C., wherein the reaction takes place in the vapor phase, followed by collection of the effluent product.

2. The process of claim 1 wherein the substrate is an ester of an N-(α-hydroxyacyl)-α-amino acid.

3. The process of claim 1 wherein the substrate is a free acid of an N-(α-hydroxyacyl)-α-amino acid.

4. The process of claim 2 wherein the equivalent alcohol of R$^3$ has a pKa of about 9 to about 14.

5. The process of claim 4 wherein the alcohol of R$^3$ is selected from a group comprising 2-chloroethanol, propargyl alcohol or phenyl alcohol derivatives.

6. The process of claim 1 wherein the substrate is dissolved in an inert solvent.

7. The process of claim 6 wherein the solvent is capable of withstanding temperatures of up to 350° C.

8. The process of claim 7 wherein the solvent is selected for the group comprising tetrahydrofuran and toluene.

9. The process of claim 1 wherein the catalyst is aluminum oxide.

10. The process of claim 9 wherein the catalyst additionally contains up to 25% silicon dioxide.

11. The process of claim 1 wherein contact time between substrate and catalyst is 0.1 to 10 seconds.

12. The process of claim 11 wherein a stream of inert gas is added to the reaction mixture.

13. The process of claim 12 wherein the inert gas is selected from the group comprising nitrogen, helium and argon.

14. The process of claim 13 wherein the inert gas is nitrogen.

15. A process for making optically active 3- and/or 6-substituted 2,5-morpholinediones of the structure:

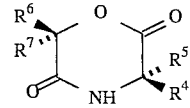

where:

a) $R^4$, $R^5$, $R^6$, and $R^7$ are independently H, $C_1$–$C_{12}$ hydrocarbyl or $C_1$–$C_{12}$ substituted hydrocarbyl and at least one is $C_1$–$C_{12}$ hydrocarbyl or $C_1$–$C_{12}$ substituted hydrocarbyl; and b) the structure contains at least one chiral center, by reacting an ester or free acid of an N-(α-hydroxyacyl)-α-amino acid substrate of the structure:

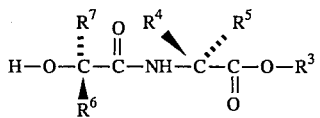

where $R^4$, $R^5$, $R^6$, and $R^7$ are defined above, $R^3$ is independently hydrogen, $C_1$–$C_{12}$ hydrocarbyl or $C_1$–$C_{12}$ substituted hydrocarbyl and the structure contains at least one chiral center and is optically active, that reaction being carried out over a fixed bed catalyst, wherein the catalyst has a surface area greater than 1 $m^2/g$, at about 150° C. to 350° C., wherein the reaction takes place in the vapor phase.

16. The process of claim 15 wherein the equivalent alcohol of $R^3$ has a pKa of between 9 and 14.

* * * * *